United States Patent [19]
Treiber et al.

[11] Patent Number: 6,121,265
[45] Date of Patent: Sep. 19, 2000

[54] HETEROCYCLIC SUBSTITUTED IMIDAZOLOQUINOXALINONES, THEIR PREPARATION AND THEIR USE

[75] Inventors: Hans-Jörg Treiber, Brühl; Wilfried Lubisch, Mannheim; Berthold Behl; Hans Peter Hofmann, both of Limburgerhof, all of Germany

[73] Assignee: BASF Aktiengesellschaft, Ludwigshafen, Germany

[21] Appl. No.: 08/809,170

[22] PCT Filed: Sep. 19, 1995

[86] PCT No.: PCT/EP95/03686

§ 371 Date: Mar. 18, 1997

§ 102(e) Date: Mar. 18, 1997

[87] PCT Pub. No.: WO96/10572

PCT Pub. Date: Apr. 11, 1996

[30] Foreign Application Priority Data

Sep. 30, 1994 [DE] Germany ................. 44 34 941
Feb. 6, 1995 [DE] Germany ................. 195 03 825

[51] Int. Cl.⁷ ............. A61K 31/495; C07D 487/04
[52] U.S. Cl. .................... 514/250; 544/346
[58] Field of Search ................ 544/346; 514/250

[56] References Cited

U.S. PATENT DOCUMENTS

| | | | |
|---|---|---|---|
| 4,291,033 | 9/1981 | Barnes et al. | 424/250 |
| 4,464,373 | 8/1984 | Barnes et al. | 544/346 |
| 5,153,196 | 10/1992 | McQuaid et al. | 514/250 |
| 5,196,421 | 3/1993 | McQuaid et al. | 514/250 |
| 5,306,819 | 4/1994 | Albaugh et al. | 544/346 |
| 5,473,073 | 12/1995 | Albaugh et al. | 544/346 |
| 5,536,718 | 7/1996 | Albright et al. | 540/558 |
| 5,741,785 | 4/1998 | Jeppesen | 514/81 |

FOREIGN PATENT DOCUMENTS

| | | |
|---|---|---|
| 2156624 | 10/1994 | Canada . |
| 260 467 | 3/1988 | European Pat. Off. . |
| 374 534 | 6/1990 | European Pat. Off. . |
| 400583 | 12/1990 | European Pat. Off. . |
| 518 530 | 12/1992 | European Pat. Off. . |
| 30 04 750 | 8/1980 | Germany . |
| WO 93/20077 | 10/1993 | WIPO . |
| WO 94/22447 | 10/1994 | WIPO . |
| WO 95/21842 | 8/1995 | WIPO . |

OTHER PUBLICATIONS

Synthesis and Excitatory Amino Acid Pharmacology of a Series . . . , McQuaid et al., J. Med. Chem. 1992, 35, 3319–3324.
Lipton, *TINS*, vol. 16, pp. 527–532 (1993).
Doble, *Therapie 50*, pp. 319–337 (1995).
Lees, *CNS Drugs 5*, pp. 51–74 (1996).

*Primary Examiner*—Emily Bernhardt
*Attorney, Agent, or Firm*—Keil & Weinkauf

[57] ABSTRACT

Imidazoloquinoxalinones of the formula

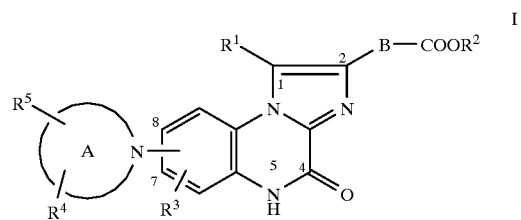

where $R^1$–$R^5$, A and B have the meanings stated in the description, and their preparation are described. The novel substances are suitable for controlling diseases.

12 Claims, No Drawings

HETEROCYCLIC SUBSTITUTED IMIDAZOLOQUINOXALINONES, THEIR PREPARATION AND THEIR USE

The present invention relates to novel imidazoloquinoxalinones with heterocyclic substituents, to processes for their preparation and to their use for controlling diseases.

What are called excitatory amino acids, especially glutamic acid, are widespread in the central nervous system. This excitatory amino acid acts as transmitter substance for glutamate receptors, of which various subtypes are known. One subtype is, for example, named after the specific agonist N-methyl-D-aspartate the NMDA receptor. This NMDA receptor has various binding sites for agonists and antagonists. The amino acid glycine likewise binds to the NMDA receptor and modulates the effect of the natural agonist glutamic acid. Antagonists at this glycine binding site may accordingly show antagonistic effects on the NMDA receptor and inhibit overexcitation of this receptor.

Two other subtypes of glutamate receptors are the AMPA receptor and the kainate receptor, which are each named after the specific agonists 2-amino-3-hydroxy-5-methyl-4-isoxazolepropionic acid (AMPA) and kainic acid. Antagonists of these receptors might, similar to the above-mentioned NMDA receptor, likewise inhibit overexcitation.

Elevated glutamate levels occur in a number of neurodegenerative diseases or psychological disturbances and may lead to overexcitation states or toxic effects in the CNS.

Antagonists of glutamate receptor subtypes may thus be used to treat these diseases. Glutamate antagonists, which include, in particular, NMDA antagonists and their modulators (such as glycine antagonists) and the AMPA antagonists, are therefore suitable for therapeutic use for neurodegenerative diseases (Huntington's chorea and Parkinson's disease), neurotoxic disturbances following hypoxia, anoxia or ischemia, as occur after stroke, or else as antiepileptics, antidepressants and anxiolytics (cf. Arzneim. Forschung 40 (1990) 511–514; TIPS, 11 (1990) 334–338 and Drugs of the Future 14 (1989) 1059–1071).

A number of imidazoloquinoxalinones of the formula II have been disclosed:

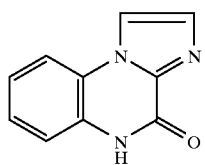

Thus, DE-A 3 004 750 and DE-A 3 004 751 describe substances which have antiallergic effects. Imidazoloquinoxalinones as phosphodiesterase inhibitors are furthermore claimed as cardiovascular agents in U.S. Pat. No. 5,166,344 (=EP 400583).

In the CNS sector, U.S. Pat. No. 5,182,386 claims imidazoloquinoxalines which are antagonists or inverse agonists of the GABA receptor and can be used to control anxiety states, sleep disturbances, convulsive states and to improve memory.

Glutamate antagonists described in numerous publications (eg. EP 374 534 and EP 260 467) are predominantly derivatives of quinoxaline-2,3-dione.

For example, WO 92/07847 relates to compounds with heterocyclic substituents in the benzenoid ring. U.S. Pat. No. 5,153,196 and U.S. Pat. No. 5,196,421, and WO 93/20077, relate to fused heterocycles, including the imidazoloquinoxalinone system. The latter also discloses substitution by heterocycles with 2–4 nitrogen atoms in the benzenoid part of the ring system.

However, the compounds published as glutamate antagonists have only alkyl, trifluoromethyl or phenyl substituents in the fused-on imidazole ring. It has now been found that substitution of the imidazoloquinoxalinone with heterocycles in the benzenoid part and carboxylic acids or esters thereof in the fused-on imidazole ring leads to novel, superior glutamate antagonists. They are therefore particularly suitable for the therapy of neurological disturbances which can be influenced thereby.

The invention relates to novel imidazoloquinoxalinones of the formula I

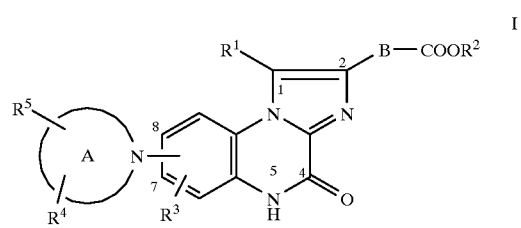

where
$R^1$ is hydrogen, branched or straight-line $C_{1-5}$-alkyl or a phenyl, pyridyl or thienyl group which is unsubstituted or substituted by one or two chlorine atoms, one trifluoromethyl, one nitro or methylenedioxy group, $R^2$ is hydrogen, $C_{1-5}$-alkyl or $C_{3-8}$-dialkylaminoalkyl, $R^3$ is a chlorine or bromine atom, a trifluoromethyl, cyano or nitro group, A is a five-membered heterocycle which is unsubstituted or substituted by $R^4$ and $R^5$ and has 1–4 nitrogen atoms or has 1–2 nitrogen atoms and one oxygen or sulfur atom, where each of the radicals $R^4$ and $R^5$, which can be identical or different, is hydrogen, $C_{1-5}$-alkyl, $C_{1-5}$-hydroxyethyl, phenyl, phenyl substituted by a chlorine atom, a trifluoromethyl or nitro group, or —COOH, —COO—$C_{1-5}$-alkyl, —$CH_2$—$NR^6R^7$ ($R^6$=H, $C_{1-5}$-alkyl, $R^7$=H, $C_{1-5}$-alkyl), —$CH_2$—NH—CO—$R^8$ ($R^8$= $C_1$–$C_5$-alkyl, phenyl, a phenyl group which is unsubstituted or substituted by a chlorine atom or a nitro or trifluoromethyl group, or a hetaryl group) or —$CH_2NHCONHR^8$ and B is a bond or a $C_{1-5}$-alkylene chain and the tautomeric and isomeric forms thereof and the physiologically tolerated salts thereof.

Preferred compounds of the formula I are those where $R^1$ is methyl, ethyl or phenyl. $R^2$ is preferably methyl or ethyl or else a hydrogen atom. When $R^2$ is hydrogen, the compounds are acids able to form salts with alkali metal and alkaline earth metal hydroxides or organic nitrogen bases. The acids can, if required, be converted into a water-soluble form by formation of a salt with, for example, sodium hydroxide or tris(hydroxymethyl)methylamine.

Preferred substituents for $R^3$ are electron-attracting groups such as nitro or trifluoromethyl in position 7.

Preferred 5-membered ring heterocycles for A are pyrrole and its derivatives. Preferred pyrrole derivatives are 3-formylpyrrole, acyl derivatives of 3-aminomethylpyrrole such as the benzoyl or pyridinecarbonyl derivatives, or those having an arylurea group, and substitution of the benzoyl group by a nitro or $CF_3$ group may be particularly emphasized. Preferred among the 5-membered ring systems with 2 nitrogen atoms are the imidazole system and its derivatives, also benzimidazole and pyrazole, and examples of 5-membered ring heterocycles with 3 and 4 nitrogen atoms are 1,2,3-triazole, 1,2,4-triazole and their derivatives, and the tetrazole system.

B is preferably a bond.

The present imidazoloquinoxalinones with heterocyclic substituents surprisingly show advantages compared with previously disclosed imidazoloquinoxalinones, in particular higher activity.

The compounds according to the invention can be prepared in a variety of ways.

8-Aminoimidazoloquinoxalinones of the formula III

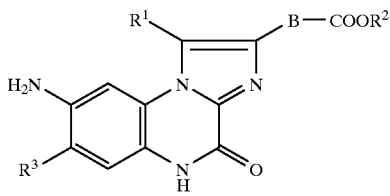

where $R^1$, $R^3$ and B have the abovementioned meanings, and $R^2$ is alkyl, are reacted with 1,4-dicarbonyl compounds or succinaldehyde derivatives, or cyclic or acyclic acetals derived therefrom, eg. formula IV

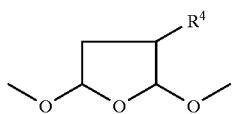

to give the pyrroles.

Compounds of the formula IV are available or can be prepared by generally known operations.

The conversion into pyrrolyl compounds is carried out by conventional processes which are detailed, for example, in C. Ferri, "Reaktionen der organischen Synthese", Thieme Verlag 1978, pp. 708 et seq., preferably in glacial acetic acid at 60–120° C. Pyrrolyl compounds V according to the invention can be prepared by using appropriately substituted diketones or acetals of the formula IV.

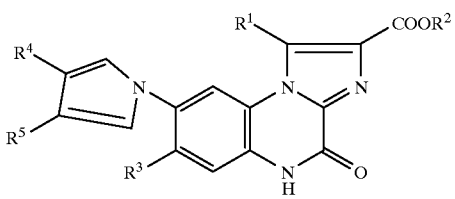

The substitution $R^4$ or $R^5$ in the pyrrolyl compounds prepared in this way can be altered in a suitable manner. Thus, for example, an aldehyde group can be converted by reduction into a hydroxyalkyl or by reductive amination into an aminoalkyl group.

The reductive amination is generally carried out at from 5 to 80° C., preferably 10 to 30° C., in the presence of reducing agents such as sodium cyanoborohydride or hydrogen in the presence of hydrogenation catalysts such as Pd/carbon, Pt/carbon or Raney nickel, expediently in polar organic solvents such as alcohols or dimethylformamide.

An aldehyde can be oxidized by conventional processes which are described, for example, in R. C. Larock "Comprehensive Organic Transformations", 1989, VCH Publisher, pp. 838 et seq., to the carboxylic acid according to the invention, and the oxidation is preferably carried out with potassium permanganate in solvents such as acetone at 25° C.

The starting compounds of the formula VI where $R^3$ has the above-mentioned meaning but is not nitro can be prepared by a process similar to that described in EP 400 583 with subsequent nitration and reduction of the nitro group as shown in Scheme 1:

Scheme 1

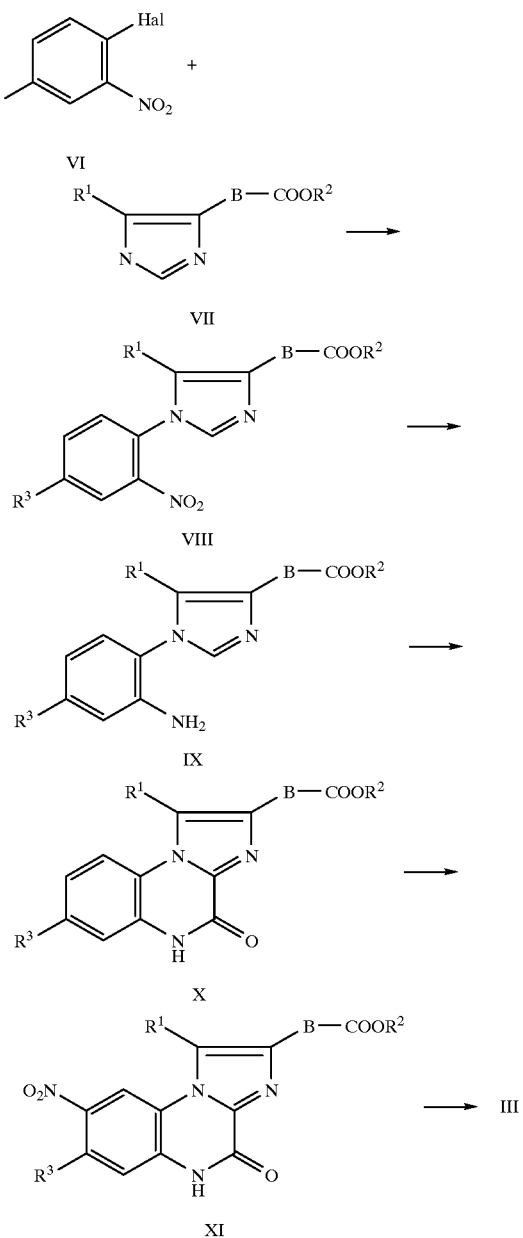

It is known that ortho-halo-substituted nitrobenzenes (VI) can be reacted with imidazoles VII which are unsubstituted on the $N_1$ nitrogen atom in suitable solvents, such as dimethyl sulfoxide, dimethylformamide or acetonitrile, at from 0 to 140° C. with addition of base, eg. potassium carbonate.

It is furthermore known that replacement of the halogen atom by 4-substituted and 4,5-disubstituted imidazoles takes place by nucleophilic attack on the least sterically hindered nitrogen atom of the imidazole to result in single products (VIII).

Reduction of the nitro compounds to aniline derivatives IX can take place in a conventional way, for example by catalytic hydrogenation with palladium or nickel catalysts or else with tin(II) chloride.

o-Halonitrobenzenes of the formula VI can be bought or can be prepared by known methods.

Ring closure to the imidazoloquinoxalinone X takes place with a doubly activated carbonic acid derivative such as phosgene, diphenyl carbonate or, preferably, N,N'-carbonyldiimidazole in an inert aprotic solvent at 150–200° C. Suitable solvents are decalin, tetralin, 1,2-dichlorobenzene or 1,3-dimethylethylene- or -propyleneurea. One process for preparing the nitro compounds XI comprises nitrating compounds X ($R^3$ as above but not nitro) with nitric acid, sulfuric acid/nitric acid or sulfuric acid/potassium nitrate at from –10° to 20°.

Reduction of the nitro group as described above results in starting compounds III suitable for preparing the pyrrolyl compounds V.

Another process for preparing the substances according to the invention comprises first reacting, as described previously, a nitrobenzene derivative XII which has two exchangeable halogen atoms with an imidazole derivative VII to give compounds VIII b, and carrying out a second reaction with a nitrogen heterocycle XIII to give compounds XIV and, after reduction of the nitro group, cyclizing the resulting compounds as described above:

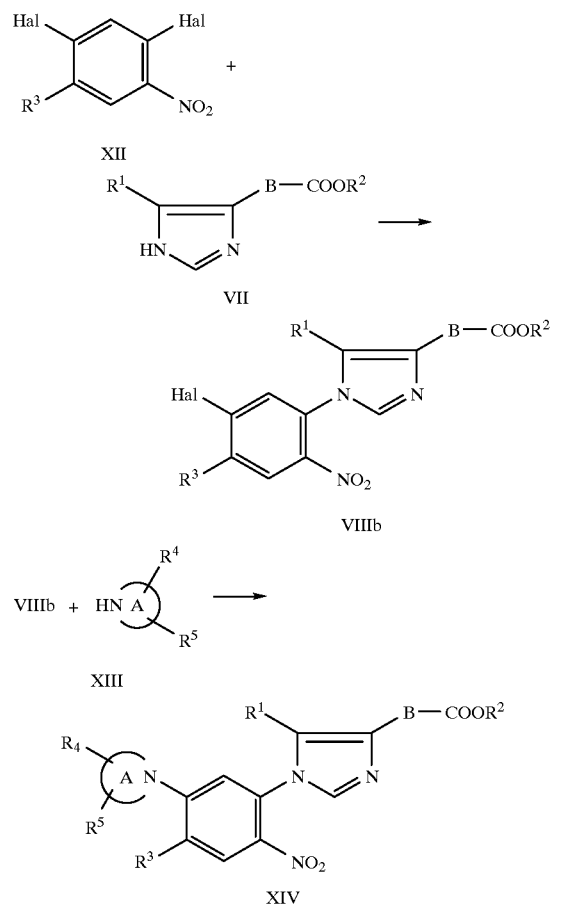

-continued $R^1$–$R^5$, A and B have the abovementioned meanings.

Particularly suitable heterocycles of the formula XIII are compounds which have an NH group which can be substituted and are derived from the nitrogen heterocycles imidazole, pyrazole, 1,2,3-triazole, 1,2,4-triazole and tetrazole. However, suitable heterocycles may also contain another hetero atom such as an oxygen or sulfur atom.

The process can, where appropriate, also be carried out by reacting an appropriate nitrobenzene XV which has two exchangeable halogen atoms and a protected amino group located in the correct position for the final cyclization first with the required heterocycle XIII and then with the required imidazole derivative VII to give XVI and, after removal of the amino protective group to give XVII, carrying out the ring closure as described previously:

Scheme 3

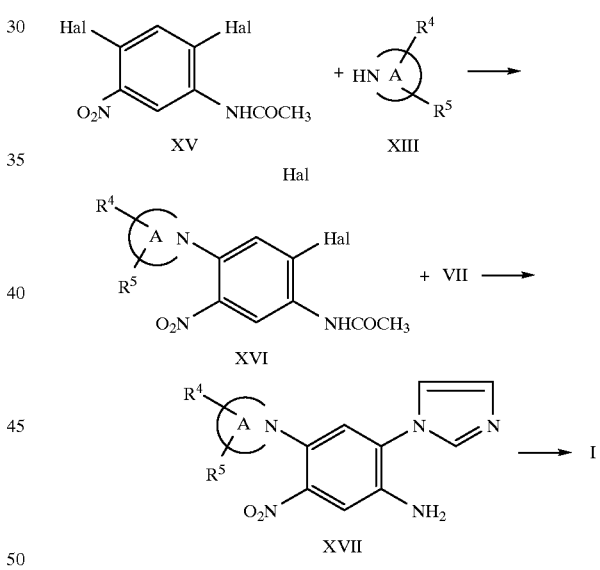

Another process for preparing the compounds I according to the invention where $R^3$ is nitro comprises initial nitration of a compound XVIII

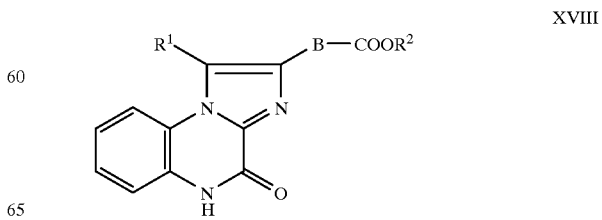

in position B (XIX), and then reduction to XX

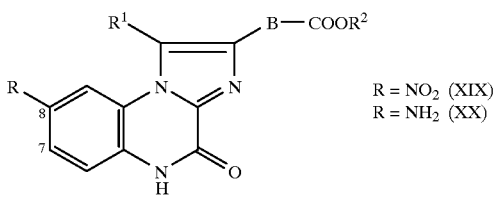

R = NO$_2$ (XIX)
R = NH$_2$ (XX)

protection of the amino group, renewed nitration in position 7 and liberation of the o-amino nitro compounds XX, which are suitable for further reaction with, for example, furan derivatives IV, by removal of the protective group.

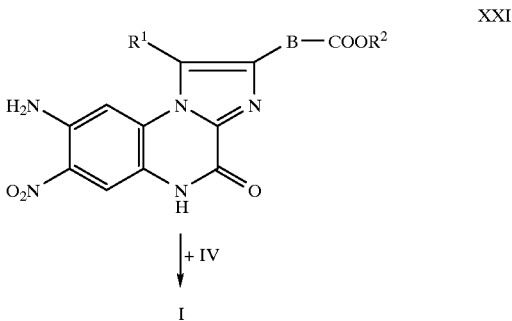

XXI

I

Compounds of the formula I where $R^1$, $R^2$, $R^3$, $R^4$, $R^5$, A and B have the abovementioned meanings can be converted by hydrolysis into acids of the formula I where $R^1$, $R^3$, $R^4$, $R^5$, A and B have the stated meanings, and $R^2$ is hydrogen.

The hydrolysis is preferably carried out under alkaline conditions, for example in the presence of an alkali metal hydroxide or of sodium bicarbonate, in a solvent such as water, a lower alcohol, tetrahydrofuran or mixtures thereof. The organic acids obtained in this way are converted where appropriate into a physiologically tolerated amine salt or metal salt. This means, in particular, salts of the alkali metals such as sodium and potassium, of the alkaline earth metals such as calcium, of other metals such as aluminum, and salts of organic bases such as morpholine, piperidine, mono-, di- and triethanolamine or tris-(hydroxymethyl)aminomethane.

The compounds according to the invention are antagonists of the excitatory amino acid glutamate, in particular antagonists of the glycine binding site of the NMDA receptor, of the AMPA receptor and of the kainate receptor.

They are suitable as pharmaceutical agents in human medicine and can be used to produce drugs for treating neurodegenerative disorders and neurotoxic disturbances of the central nervous system and for producing spasmolytics, antiepileptics, anxiolytics and antidepressants.

The pharmacological activity of the compounds I was investigated on isolated membrane material from rat cerebra. For this purpose, the membranes were incubated in the presence of the compounds according to the invention with the radiolabeled substances $^3$H-2-amino-3-hydroxy-5-methyl-4-isoxazolepropionic acid ($^3$H-AMPA), [$^3$H]-glycine and [$^3$H]-kainate, which bind specifically to AMPA, NMDA and kainate receptors respectively. After this incubation, the radioactivity measured by scintillation counting was used to determine the extent of the binding of the said radioactive receptor ligands to the membrane receptors. The affinity of the compounds according to the invention for the relevant receptors was calculated from the concentration-dependent displacement of this binding by the compounds according to the invention. The dissociation constant $K_I$ (as measure of the affinity) was determined by iterative non-linear regression analysis using the Statistical Analysis System (SAS), similar to the ligand program of P. J. Munson and D. Rodbard (Analytical Biochem. 107 (1980) 220, Ligand: Versatile Computerized Approach for Characterization of Ligand Binding Systems).

The following in vitro investigations were carried out:

1. Binding of $^3$H-2-amino-3-hydroxy-5-methyl-4-isoxazolepropionic acid ($^3$H-AMPA)

To prepare the membrane material, freshly removed rat cerebra were homogenized with 15 times the volume of a buffer solution A composed of 30 mM α,α,α-tris (hydroxymethyl)methylamine hydrochloride (TRIS-HCl) and 0.5 mM ethylenediaminetetraacetic acid (EDTA), pH 7.4, using an Ultra-Turax®. The suspension was centrifuged at 48000 g for 20 min. After removal of the supernatant liquid, the protein-containing membrane material contained in the sediment was washed three times by suspension in buffer solution A and subsequent centrifugation at 48 000 g for 20 minutes each time. The membrane material was then suspended in 15 times the volume of buffer solution A and incubated at 37° C. for 30 min. The protein material was subsequently washed twice by centrifugation and suspension and stored at −70° C. until used.

For the binding assay, the protein material was thawed at 37° C. and washed twice by centrifugation at 48 000 g (20 min) and subsequent suspension in buffer solution B composed of 50 mM TRIS-HCl, 0.1M potassium thiocyanate and 2.5 mM calcium chloride, pH 7.1. Subsequently, 0.25 mg of membrane material, 0.1 μCi of $^3$H-AMPA (60 Ci/mmol) and compound I were dissolved in 1 ml of buffer solution B and incubated on ice for 60 min. The incubated solution was filtered through a CF/B filter (from Whatman) which had previously been treated with a 0.5% strength aqueous solution of polyethyleneimine for at least 2 hours. The membrane residue was then washed with 5 ml of cold buffer solution B to separate bound and free $^3$H-AMPA from one another. After measurement of the radioactivity of bound $^3$H-AMPA in the membrane material by scintillation counting, the $K_I$ was determined by regression analysis of the displacement plots.

2. Binding of [$^3$H]-glycine

To prepare the membranes for the $^3$H-glycine binding assay, freshly removed rat hippocampi were homogenized in 10 times the volume of preparation buffer (50 mM tris-HCl, 10 mM EDTA) using a Potter homogenizer. The homogenate was centrifuged at 48000×g for 20 min. The supernatant was discarded, and the membranes contained in the pellet were washed 2× by resuspension and centrifugation at 48000×g (20 min each time). The resuspended membranes were frozen in liquid nitrogen and thawed again at 37° C. After another washing step, the membrane suspension was incubated in a shaking water bath at 37° C. for 15 min. After a further 4 washing steps (in each case centrifugation at 48000×g for 20 minutes and resuspension in preparation buffer), the membranes were stored at −70° C. until used further.

The frozen membranes were thawed at 37° C. and washed 2× by centrifugation at 48000×g (20 min) and subsequent resuspension in binding buffer (50 mM tris-HCl pH 7.4; 10 mM MgCl$_2$). An incubation mixture contained 0.25 mg of protein (membranes), 25 nM $^3$H-glycine (16 Ci/mMol) and the substances to be tested in a total of 0.5 ml of binding buffer. The non-specific binding was determined adding 1 mM glycine. After incubation at 4° C. for 60 min, separation of bound and free ligand from one another took place by filtration through GF/B filters and subsequent washing with about 5 ml of ice-cold binding buffer. The radioactivity remaining on the filters was determined by liquid scintillation counting. The dissociation constants were calculated from the displacement plots using an iterative non-linear fitting program or in accordance with the equation of Cheng and Prusoff.

3. Binding of [$^3$H]-kainate

To prepare the membranes for the [$^3$H]-kainate binding assay, freshly removed rat cerebra were homogenized in 15 times the volume of preparation buffer (30 mM Tris-HCl pH 7.4, 0.5 mM EDTA) using an Ultra-Turrax®. The homogenate was centrifuged at 48000×g for 20 min. The supernatant was discarded, and the membranes contained in the pellet were washed a total of 3× by resuspension in preparation buffer and centrifugation at 48000×g (20 min each time). After the third washing step, the membranes were incubated at 37° C. The membranes were then washed 2× by centrifugation and resuspension and stored at −70° C. until used further.

The frozen membranes were thawed at 37° C., suspended in binding buffer (50 mM tris-HCl pH 7.4) and centrifuged at 48000×g for 20 min. The membranes present in the pellet were resuspended in binding buffer. An incubation mixture contained 0.25 mg of protein (membranes), 0.058 μCi of [$^3$H]-kainate (58 Ci/mmol) and the substances to be tested in a total of 1 ml of binding buffer. The non-specific binding was determined in the presence of 0.1 mM glutamate. After incubation on ice for 60 minutes, separation of bound and free ligand took place by filtration through CF/B filters and subsequent washing with 5 ml of ice-cold binding buffer. The CF/B filters had previously been treated with 0.5% polyethyleneimine for at least 2 h. The analysis of the displacement plots and calculation of the dissociation constants took place using a non-linear fitting program or in accordance with the equation of Cheng and Prusoff.

The novel compounds perform very well in these assays.

The pharmaceutical compositions according to the invention contain a therapeutically effective amount of the compounds I in addition to conventional pharmaceutical ancillary substances. The agents can be present in conventional concentrations for local external use, eg. in dusting powders and ointments. As a rule, the agents are present in an amount of from 0.0001 to 1% by weight, preferably 0.001 to 0.1% by weight.

For internal use, the preparations are administered in single doses. From 0.1 to 100 mg are administered per kg of body weight in a single dose. The compositions can be administered in one or more doses each day depending on the nature and severity of the disorders.

The pharmaceutical compositions according to the invention contain, besides the agent, the conventional excipients and diluents appropriate for the required mode of administration. Pharmaceutical ancillary substances which can be used for local external use are, for example, ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable examples for internal use are lactose, propylene glycol, ethanol, starch, talc and polyvinylpyrrolidone.

It is furthermore possible for antioxidants such as tocopherol and butylated hydroxyanisole, and butylated hydroxytoluene, flavoring additives, stabilizers, emulsifiers and lubricants to be present.

The substances present in the composition in addition to the agent, and the substances used for producing the pharmaceutical composition are toxicologically acceptable and compatible with the agent in each case. The pharmaceutical compositions are produced in a conventional way, eg. by mixing the agent with the conventional excipients and diluents.

The pharmaceutical compositions can be administered in various ways, such as orally, parenterally, subcutaneously, intraperitoneally and topically. Thus, possible presentations are tablets, emulsions, infusion and injection solutions, pastes, ointments, gels, creams, lotions, dusting powders and sprays.

EXAMPLES

Example 1

Ethyl 4,5-dihydro-1-methyl-8-(1-pyrrolyl)-7-trifluoromethyl-4-oxoimidazolo[1,2-a]quinoxaline-2-carboxylate a. 1-(2-Nitro-4-trifluoromethylphenyl)-4-carbethoxy-5-methylimidazole A mixture of 10.45 g (0.05 mol) of 2-fluoro-4-trifluoromethylnitrobenzene, 7.7 g (0.05 mol) of 4(5)-carbethoxy-5(4)-methylimidazole and 13.8 g of potassium carbonate in 100 ml of acetonitrile was refluxed for 4 h.

1000 ml of water were added to the cooled reaction mixture, the mixture was extracted with 250 ml of methylene chloride, and the methylene chloride phase was dried with magnesium sulfate. The dried solution was evaporated, and the residue was induced to crystallize by trituration with ether.

Yield: 11.4 g (66% of theory); Melting point: 142–144° C.

b. 1-(2-Amino-4-trifluoromethylphenyl)-4-carbethoxy-5-methylimidazole 11.6 g (0.034 mol) of compound a. described above were hydrogenated with 2 g of palladium/carbon catalyst (10% Pd) in 100 ml of ethanol under atmospheric pressure at room temperature. After hydrogen uptake ceased, the catalyst was removed from the solution which was then evaporated under reduced pressure, and the residue was induced to crystallize with a little ether.

Yield: 9.8 g (93% of theory); Melting point: 189–190° C.

c. Ethyl 4,5-dihydro-1-methyl-7-trifluoromethyl-4-oxoimidazolo[1,2-a]quinoxaline-2-carboxylate 7.3 g (0.0233 mol) of compound b. described above and 4.2 g (0.0259 mol) of N,N'-carbonyldiimidazole in 100 ml of 1,2-dichlorobenzene were boiled with stirring for 2.5 h. After cooling, the solid was filtered off with suction and washed with acetone/ether.

Yield: 5.1 g (64.5% of theory); Melting point: 270–271° C.

d. Ethyl 4,5-dihydro-1-methyl-8-nitro-7-trifluoromethyl-4-oxoimidazolo[1,2-a]quinoxaline-2-carboxylate 5.0 g (0.015 mol) of compound c. described above were nitrated with a mixture of 50 ml of concentrated sulfuric acid and 50 ml of nitric acid (d=1.50) at room temperature for 72 h and subsequently at 60° C. for 1 h. The mixture was cooled and then poured onto ice, and the product was filtered off with suction and washed with water.

Yield: 3.9 g (70% of theory); Melting point: 284–286° C.

e. Ethyl 8-amino-4,5-dihydro-1-methyl-7-trifluoromethyl-4-oxoimidazolo[1,2-a]quinoxaline-2-carboxylate 12 g (0.031 mol) of compound d. described above were dissolved in 200 ml of boiling glacial acetic acid and subsequently 15 g of iron powder were introduced in portions over the course of 15 min. After 30 min, the precipitate was filtered off with suction and washed with acetic acid, water and methanol.

Yield: 10 g (91% of theory); Melting point: 300° C.

f. 1.5 g (0.0042 mol) of compound e. described above were taken up in 30 ml of glacial acetic acid, 1.12 g (0.085 mol) of 2,5-dimethoxytetrahydrofuran were added, and the mixture was rapidly heated to boiling in a preheated oil bath until a solution was obtained. The mixture was rapidly cooled after 5 min, and the precipitate was filtered off with suction and washed with acetic acid and ether.

Yield: 0.75 g (44% of theory); Melting point: 290–295° C.; $C_{19}H_{15}F_3N_4O_3$
Further compounds were prepared as in process 1f using the following 2,5-dimethoxytetrahydrofuran derivatives substituted in position 3.
2,5-Dimethoxytetrahydrofuran derivatives:
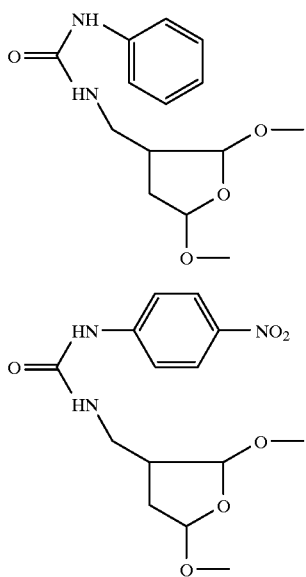
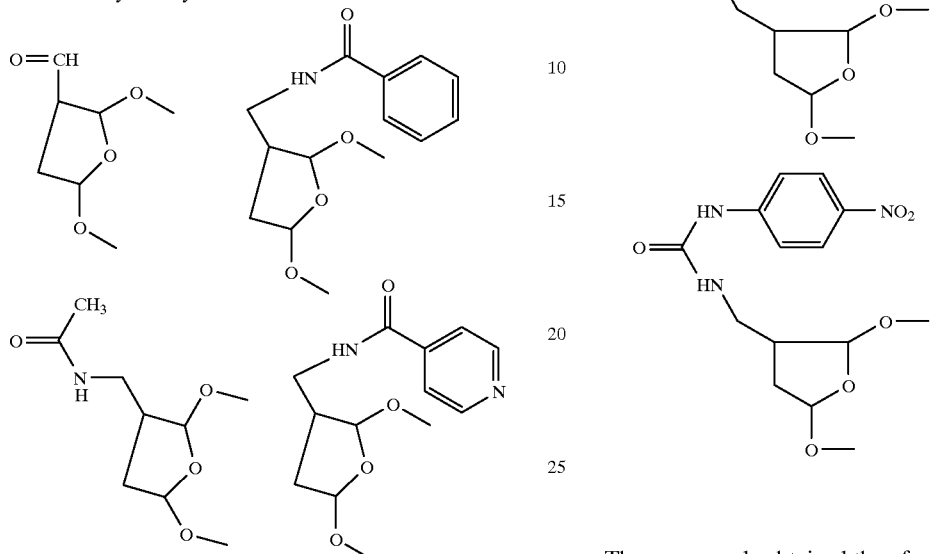
The compounds obtained therefrom are shown in Table I:
| Ex. No. | Structural formula | Molecular formula | Melting point |
|---|---|---|---|
| 2 | | $C_{20}H_{15}F_3N_4O_4$ | 292–296° C. |
| 3 | | $C_{27}H_{23}F_3N_6O_4$ | >300° C. |

-continued

| Ex. No. | Structural formula | Molecular formula | Melting point |
|---|---|---|---|
| 4 | | $C_{27}H_{23}F_3N_7O_6$ | 225–230° C. |
| 5 | | $C_{22}H_{20}F_3N_5O_4$ | 198–200° C. |
| 6 | | $C_{22}H_{19}F_3N_4O_4$ | 235–239° C. |
| 7 | | $C_{26}H_{21}F_3N_6O_4$ | 268–270° C. |
| 8 | | $C_{27}H_{22}F_3N_5O_4$ | 230–231° C. |

Example 9

Ethyl 4,5-dihydro-8-(2,5-dimethyl-1-pyrrolyl)-1-methyl-7-triluoromethyl-4-oxoimidazolo[1,2-a]quinoxaline-2-carboxylate 1.0 g (0.0028 mol) of the compound of Example 1e was boiled together with 2 g of acetonylacetone in 25 ml of acetic acid, a solution being obtained after 5 min. After heating for a further 10 min, the mixture was cooled, and the precipitate was filtered off with suction, washed with ether and dried under reduced pressure.

Yield: 0.9 g (75% of theory); Melting point >300° C.; $C_{21}H_{19}F_3N_4O_3$

Example 10

4,5-Dihydro-1-methyl-8-(1-pyrrolyl)-7-trifluoromethyl-4-oxoimidazolo[1,2-a]-quinoxaline-2-carboxylic acid 0.5 g of the ester prepared in Example 1f was dissolved in a solution of 1 g of LiOH in 50 ml of water by brief heating at 80° C. After some hours, the mixture was acidified to pH 5 with acetic acid, and the precipitate was filtered off with suction and dried under reduced pressure.

Yield: 0.4 g (86% of theory); Melting point >300° C.; $C_{21}H_{19}F_3N_4O_3$

The following compounds were obtained in a similar manner from the esters of Examples 2–9:

| Ex. No. | Structural formula | Molecular formula | Melting point |
|---------|-------------------|-------------------|---------------|
| 11 | | $C_{18}H_{11}F_3N_4O_4$ | >300° C. |
| 12 | | $C_{25}H_{19}F_3N_6O_4$ | >300° C. |
| 13 | | $C_{26}H_{21}F_3N_6O_4$ | >300° C. |

-continued

| Ex. No. | Structural formula | Molecular formula | Melting point |
| --- | --- | --- | --- |
| 14 | | $C_{26}H_{20}F_3N_7O_6$ | 290–295° C. |
| 15 | | $C_{25}H_{18}F_3N_7O_6$ | >300° C. |
| 16 | | $C_{25}H_{19}F_3N_6O_4$ | >300° C. |
| 17 | | $C_{19}H_{15}F_3N_4O_3$ | >300° C. |

| Ex. No. | Structural formula | Molecular formula | Melting point |
|---|---|---|---|
| 18 | (structure) | $C_{20}H_{15}F_3N_4O_4$ | >300° C. |
| 19 | (structure) | $C_{25}H_{18}F_3N_5O_4$ | 298–300° C. |

20. 4,5-Dihydro-8-(1-imidazolyl)-1-methyl-7-trifluoromethyl-4-oxoimidazolo[1,2-a]quinoxaline-2-carboxylic acid a. 1-(5-Chloro-2-nitro-4-trifluoromethylphenyl)-4-carbethoxy-5-methylimidazole prepared as in Example 1a from 2,4-dichloro-5-nitrobenzotrifluoride and 4(5)-carbethoxy-5(4)-methylimidazole Melting point 118–119° C.; $C_{14}H_{11}ClF_3N_3O_4$ b. 4-(4-Carbethoxy-5-methyl-1-imidazolyl)-2-(1-imidazolyl)-5-nitrobenzotrifluoride 5 g (0.013 mol) of the product prepared in Example 1a and 1.8 g (0.026 mol) of imidazole in 100 ml of acetonitrile were refluxed for 120 h. The solvent was then removed by distillation, the residue was treated with ethyl acetate and water, and the solvent phase was separated off, washed once more with water, dried and evaporated. The product crystallized after trituration of the residue with a 99:1 mixture of diisopropyl ether in THF.

Melting point 160–162° C.; $C_{17}H_{14}F_3N_5O_4$ c. 2-(4-Carbethoxy-5-methyl-1-imidazolyl)-4-(1-imidazolyl)-5-trifluoromethylaniline 3.5 g of the product from Example 1b in 50 ml of acetic acid were heated to boiling and then 5.6 g of iron powder were added in portions. After 20 min, the mixture was filtered with suction, the solution was evaporated under reduced pressure, water was added and the mixture was extracted twice with ethyl acetate. The extract was then washed with sodium carbonate solution until free of acid, the solution was dried and evaporated, and the residue was digested with ether.

Yield: 1.8 g (55% of theory) Melting point 265–266° C.

d. Preparation of the final product 0.7 g (0.002 mol) of the compound obtained in 20c and 0.5 g of 1,1'-carbonyldiimidazole in 50 ml of 1,2-dichlorobenzene were refluxed for 2 h. The precipitate obtained after cooling was filtered off with suction and washed with a hot methanol/isopropanol mixture.

The following was obtained: Yield 0.2 g (25% of theory); Melting point 265–270° C.; $C_{18}H_{14}F_3N_5O_3$ The following were obtained in a similar way using different starting compounds:

21. Ethyl 4,5-dihydro-1-methyl-8-(2-methyl-1-imidazolyl)-7-trifluoromethyl-4-oxoimidazolo[1,2-a]quinoxaline-2-carboxylate Melting point >300° C.; $C_{19}H_{15}F_3N_4O_3$ 22. Ethyl 4,5-dihydro-1-methyl-8-(1,2,4-triazol-1-yl)-7-trifluoromethyl-4-oxoimidazolo[1,2-a]quinoxaline-2-carboxylate Melting point 291–293° C.; $C_{17}H_{13}F_3N_6O_3$ The following compounds were obtained from the compounds of Examples 19–21 by hydrolysis with lithium hydroxide as in Example 10:

23. 4,5-Dihydro-8-(1-imidazolyl)-1-methyl-7-trifluoromethyl-4-oxoimidazolo[1,2-a]quinoxaline-2-carboxylic acid Melting point 291–293° C.; $C_{17}H_{13}F_3N_6O_3$ 24. 4,5-Dihydro-1-methyl-8-(2-methyl-1-imidazolyl)-7-trifluoromethyl-4-oxoimidazolo[1,2-a]quinoxaline-2-carboxylic acid Melting point >300° C.; $C_{17}H_{12}F_3N_5O_3$ 25. 4,5-Dihydro-1-methyl-8-(1,2,4-triazol-1-yl)-7-trifluoromethyl-4-oxoimidazolo[1,2-a]quinoxaline-2-carboxylic acid Melting point >300° C.; $C_{17}H_{12}F_3N_5O_3$ 26. 4,5-Dihydro-1-ethyl-8-(1-imidazolyl)-7-trifluoromethyl-4-oxoimidazolo[1,2-a]quinoxaline-2-carboxylic acid Melting point >300° C.; $C_{17}H_{12}F_3N_5O_3$ 27. Ethyl 4,5-dihydro-8-(3-formyl-1-pyrrolyl)-1-methyl-7-nitro-4-oxoimidazolo[1,2-a]quinoxaline-2-carboxylate.

a. Preparation of the starting material:

Ethyl 4,5-dihydro-1-methyl-4-oxoimidazolo[1,2-a]quinoxaline-2-carboxylate was prepared by reacting 2-fluoronitrobenzene with 4(5)-carbethoxy-5(4)methylimidazole, followed by hydrogenation and subsequent ring closure with N,N'-carbonyldiimidazole.

b. Ethyl 4,5-dihydro-1-methyl-8-nitro-4-oxoimidazolo[1,2-a]quinoxaline-2-carboxylate 25 g (0.09 mol) of the substance described above under a) were introduced in portions into 300 ml of 100% strength nitric acid while stirring at 0–5° C. After 15 min, the mixture was poured onto ice and filtered with suction, and the residue was treated with acetone to obtain crystals of the product.

Yield: 26 g (82% of theory); Melting point >300° C.; $C_{14}H_{12}N_4O_5$ c. Ethyl 4,5-dihydro-8-acetamido-1-methyl-4-oxoimidazolo-[1,2-a]quinoxaline-2-carboxylate The compound described above under b) was reduced with iron powder in boiling acetic acid Yield: 66% of theory; Melting point >300° C.; $C_{16}H_{16}N_4O_4$ d. Ethyl 4,5-dihydro-8-acetamido-1-methyl-7-nitro-4-oxoimidazolo[1,2-a]quinoxaline-2-carboxylate 1 g of the compound described under d) was nitrated by introduction in portions into 25 ml of 100% strength nitric acid at 20° C. followed by stirring for 5 min.

Yield: 0.8 g (70% of theory); Melting point >300° C.; $C_{16}H_{15}N_5O_6$ e. Ethyl 4,5-dihydro-8-amino-1-methyl-7-nitro-4-oxoimidazolo[1,2-a]quinoxaline-2-carboxylate The preceding compound d) was selectively hydrolyzed with hydrochloric acid by initially heating the compound to 70° C. and then slowly cooling to room temperature.

Yield: 1.4 g (35% of theory); Melting point >300° C.; $C_{14}H_{13}N_5O_5$ f. Preparation of the final product 1.0 g (0.003 mol) of the compound obtained in e) was reacted with 1.0 g of 2,5-dimethoxy-3-formyltetrahydrofuran in boiling glacial acetic acid as in Example 1f.

Yield: 0.3 g (24% of theory); Melting point 220–225° C.; $C_{19}H_{15}N_5O_6$

28. Ethyl 4,5-dihydro-1-methyl-8-(2-methyl-1-imidazolyl)-7-nitro-4-oxoimidazolo[1,2-a]quinoxaline-2-carboxylate a. 5-Acetamido-4-fluoro-2-(2-methyl-1-imidazolyl) nitrobenzene 3 g (0.0138 mol) of 5-acetamido-2,4-difluoro-1-nitrobenzene were reacted with 1.1 g (0.0135 mol) of 2-methylimidazole and 5 g of potassium carbonate in 50 ml of acetonitrile by stirring at 50° C. for 72 h. For the working up, the reaction mixture was filtered with suction, evaporated under reduced pressure and purified by column chromatography (silica gel, methylene chloride ±5% methanol).

Yield: 1.0 g (26% of theory); Melting point 209–210° C. (from isopropanol); $C_{12}H_{11}FN_4O_3$ b. 5-Amino-2-(2-methyl-1-imidazolyl)-4-(4-carbethoxy-5-methyl-1-imidazolyl)nitrobenzene 6.0 g (0.022 mol) of the compound described under a) were reacted with 3.4 g (0.022 mol) of 4(5)-carbethoxy-5(4)-methylimidazole and 6 g of potassium carbonate in 100 ml of DMF by stirring at 120° C. for 2 h. For working up, the mixture was filtered with suction, the solution was evaporated under reduced pressure, water was added and the mixture was extracted with methylene chloride. The residue obtained after drying and evaporation was recrystallized from isopropanol (Yield 3.5 g=39%) and then stirred with 100 ml of hydrochloric acid at 60° C. for 4 h. For working up, the hydrochloric acid was substantially removed by distillation under reduced pressure, and the product was neutralized with dilute ammonia at 0° C. and extracted with methylene chloride. The residue was purified by column chromatography.

Yield: 1 g c. 1.0 g of the compound described under b) was reacted with 0.6 g of N,N'-carbonyldiimidazole in 50 ml of 1,2-dichlorobenzene by stirring at 160–170° C. for 2 h. After cooling to 50° C., the solution was decanted off the precipitate, and the residue was treated with hot acetone and filtered off with suction. The filtrate was evaporated to result in 0.1 g of the desired compound.

Melting point 265–270° C.; $C_{18}H_{16}N_6O_5$

29. Ethyl 4,5-dihydro-1-methyl-8-(1-imidazolyl)-7-nitro-4-oxoimidazolo[1,2-a]quinoxaline-2-carboxylate a. 5-Amino-4-fluoro-2-(1-imidazolyl)nitrobenzene 12 g (0.068 mol) of 5-amino-2,4-difluoronitrobenzene were slowly added at 0° C. to a solution of 4.7 g of imidazole (0.069 mol) and 2.1 g of sodium hydride (80% in oil; 0.07 mol) and then stirred at this temperature for several hours. The mixture was then diluted with water and extracted several times with methylene chloride. The residue after drying and evaporation was recrystallized from isopropanol.

Yield: 7.1 g (45% of theory); Melting point 211–212° C.

b. 5-Amino-2-(1-imidazolyl)-4-(4-carbethoxy-5-methyl-1-imidazolyl)nitrobenzene 4.2 g (0.027 mol) of 4(5)-carbethoxy-5(4)-methylimidazole were pretreated with 0.82 g of sodium hydride (80% in oil; 0.027 mol) in 30 ml of DMF for 1 h and then 6.1 g (0.027 mol) of the compound described above under a. were added and the mixture was stirred overnight. It was then heated at 50° C. for 1 h before working up. For working up, water was added, and then 3 ml of acetic acid were added and the mixture was extracted with methylene chloride, followed by drying and evaporation. The compound was obtained as crystals after treatment with ether/isopropanol (95+5).

Yield: 4.2 g (42% of theory); Melting point 213–215° C.

c. Preparation of the final product 1.0 g of the compound described under b. was reacted as described under Example 28c, and the compound according to the example was obtained in a yield of 0.3 g (24% of theory).

Melting point 328–330° C. $C_{18}H_{13}N_5O6$

The following were obtained by hydrolysis of the compounds of Example 28 and 29 with lithium hydroxide as in Example 10:

30. 4,5-Dihydro-1-methyl-8-(1-imidazolyl)-7-nitro-4-oxoimidazolo[1,2-a]quinoxaline-2-carboxylic acid Melting point >300° C.; $C_{15}H_{10}N_6O_5$ 31. 4,5-Dihydro-1-methyl-8(2-methyl-1-imidazolyl)-7-nitro-4-oxoimidazolo[1,2-a]quinoxaline-2-carboxylic acid Melting point >300° C.; $C_{16}H_{12}N_6O_5$ 32. 4,5-Dihydro-8-(3-formyl-1-pyrrolyl)-1-methyl-7-nitro-4-oxoimidazolo[1,2-a]quinoxaline-2-carboxylic acid The above compound was obtained by hydrolysis of the compound of Example 27 with lithium hydroxide as in Example 10.

Melting point >300° C.; $C_{17}H_{11}N_5O_6$

We claim:

1. An imidazoloquinoxalinone of the formula I

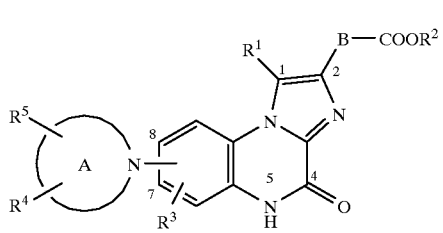

where $R^1$ is hydrogen, branched or straight-line $C_{1-5}$-alkyl or a phenyl, pyridyl or thienyl group which is unsubstituted or substituted by one or two chlorine atoms, one trifluoromethyl, one nitro or methylenedioxy group, $R^2$ is hydrogen, $C_{1-5}$-alkyl or $C_{3-8}$-dialkylaminoalkyl, $R^3$ is a chlorine or bromine atom, a trifluoromethyl, cyano or nitro group, A is pyrrolyl, or 1,2,4-triazolyl, $R^4$ and $R^5$, which can be identical or different, are hydrogen, $C_{1-5}$-alkyl, $C_{1-5}$-hydroxyethyl, phenyl, phenyl substituted by a chlorine atom, a trifluoromethyl or nitro group, or —COOH, —COO—$C_{1-5}$-alkyl, —$CH_2$—$NR^6R^7$, —$CH_2$—NH—CO—$R^8$ or —$CH_2$—$NHCONHR^8$, where $R^6$ is hydrogen or $C_{1-5}$-alkyl, $R^7$ is hydrogen or $C_{1-5}$-alkyl, and $R^8$ is $C_{1-5}$-alkyl, a phenyl group which is unsubstituted or substituted by a chlorine atom or a nitro or trifluoromethyl group, or a pyridyl group, and B is a bond or a $C_{1-5}$-alkylene chain, or a tautomeric form thereof or a physiologically tolerated salt thereof.

2. A pharmaceutical composition for oral, parenteral or intraperitoneal use, containing per single dose from 0.1 to 100 mg/kg of body weight of at least one imidazoloquinoxalinone I as defined in claim 1, in addition to conventional pharmaceutical ancillary substances.

3. A pharmaceutical composition for intravenous use, containing from 0.001 to 10% by weight of at least one imidazoloquinoxalinone I as defined in claim 1, in addition to conventional pharmaceutical ancillary substances.

4. A method for controlling spasms, epilepsy, anxiety or depression due to neurodegenerative disorders and neurotoxic disturbances of the central nervous system which comprises administering to a patient in need thereof an effective amount of an imidazoloquinoxalinone I as defined in claim 1.

5. An imidazoloquinoxalinone of the formula I (I)

where $R^1$ is hydrogen, branched or straight-line $C_{1-5}$-alkyl or a phenyl, pyridyl or thienyl group which is unsubstituted or substituted by one or two chlorine atoms, one trifluoromethyl, one nitro or methylenedioxy group, $R^2$ is hydrogen, $C_{1-5}$-alkyl or $C_{3-8}$-dialkylaminoalkyl, $R^3$ is a chlorine or bromine atom, a trifluoromethyl, cyano or nitro group, A is pyrrolyl, $R^4$ and $R^5$, which can be identical or different, are hydrogen, $C_{1-5}$-alkyl, $C_{1-5}$-hydroxyethyl, phenyl, phenyl substituted by a chlorine atom, a trifluoromethyl or nitro group, or —COOH, —COO—$C_{1-5}$-alkyl, —$CH_2$—$NR^6R^7$, —$CH_2$—NH—CO—$R^8$ or —$CH_2$—$NHCONHR^8$, where $R^6$ is hydrogen or $C_{1-5}$-alkyl, $R^7$ is hydrogen or $C_{1-5}$-alkyl, and $R^8$ is $C_{1-5}$-alkyl, a phenyl group which is unsubstituted or substituted by a chlorine atom or a nitro or trifluoromethyl group, or a pyridyl group, and B is a bond or a $C_{1-5}$-alkylene chain, or a tautomeric form thereof or a physiologically tolerated salt thereof.

6. A pharmaceutical composition for oral, parenteral or intraperitoneal use, containing per single dose from 0.1 to 100 mg/kg of body weight of at least one imidazoloquinoxalinone I as defined in claim 5, in addition to conventional pharmaceutical ancillary substances.

7. A pharmaceutical composition for intravenous use, containing from 0.001 to 10% by weight of at least one imidazoloquinoxalinone I as defined in claim 5, in addition to conventional pharmaceutical ancillary substances.

8. A method for controlling spasms, epilepsy, anxiety or depression due to neurodegenerative disorders and neurotoxic disturbances of the central nervous system which comprises administering to a patient in need thereof an effective amount of an imidazoloquinoxalinone I as defined in claim 5.

9. An imidazoloquinoxalinone of the formula I (I)

where $R^1$ is hydrogen, branched or straight-line $C_{1-5}$-alkyl or a phenyl, pyridyl or thienyl group which is unsubstituted or substituted by one or two chlorine atoms, one trifluoromethyl, one nitro or methylenedioxy group, $R^2$ is hydrogen, $C_{1-5}$-alkyl or $C_{3-8}$-dialkylaminoalkyl, $R^3$ is a chlorine or bromine atom, a trifluoromethyl, cyano or nitro group, A is 1,2,4-triazolyl, $R^4$ and $R^5$, which can be identical or different, are hydrogen, $C_{1-5}$-alkyl, $C_{1-5}$-hydroxyethyl, phenyl, phenyl substituted by a chlorine atom, a trifluoromethyl or nitro group, or —COOH, —COO—$C_{1-5}$-alkyl, —$CH_2$—$NR^6R^7$, —-$CH_2$—NH—CO—$R^8$ or —$CH_2$—$NHCONHR^8$, where $R^6$ is hydrogen or $C_{1-5}$-alkyl, $R^7$ is hydrogen or $C_{1-5}$-alkyl, and $R^8$ is $C_{1-5}$-alkyl, a phenyl group which is unsubstituted or substituted by a chlorine atom or a nitro or trifluoromethyl group, or a pyridyl group, and B is a bond or a $C_{1-5}$-alkylene chain, or a tautomeric form thereof or a physiologically tolerated salt thereof.

10. A pharmaceutical composition for oral, parenteral or intraperitoneal use, containing per single dose from 0.1 to 100 mg/kg of body weight of at least one imidazoloquinoxalinone I as defined in claim 9, in addition to conventional pharmaceutical ancillary substances.

11. A pharmaceutical composition for intravenous use, containing from 0.001 to 10% by weight of at least one imidazoloquinoxalinone I as defined in claim 9, in addition to conventional pharmaceutical ancillary substances.

12. A method for controlling spasms, epilepsy, anxiety or depression due to neurodegenerative disorders and neurotoxic disturbances of the central nervous system which comprises administering to a patient in need thereof an effective amount of an imidazoloquinoxalinone I as defined in claim 9.

* * * * *